United States Patent [19]

Bonfils et al.

[11] 4,164,571
[45] Aug. 14, 1979

[54] MEDICAMENT WHICH ANTAGONIZES THE ACTION OF GASTRIN AND RELATED POLYPEPTIDES

[75] Inventors: Serge J. E. Bonfils; Juliette M. Dubrasquet, both of Paris; Pierre Fromageot, Versailles; Jean P. Girma, Gif sur Yvette; Miguel Lewin, Asnieres; Jean L. Morgat, Paris, all of France

[73] Assignees: Commissariat a l'Energie Atomique; Institut National de la Sante et de la Recherche Medicale, both of Paris, France

[21] Appl. No.: 835,394

[22] Filed: Sep. 21, 1977

[30] Foreign Application Priority Data

Sep. 21, 1976 [FR] France .................... 76 2833

[51] Int. Cl.$^2$ .................... A61K 37/00; C07C 103/52
[52] U.S. Cl. .................... 424/177; 260/112.5 R
[58] Field of Search .................... 260/112.5 R; 424/177

[56] References Cited

U.S. PATENT DOCUMENTS

| 3,896,103 | 7/1975 | Hardy et al. | 260/112.5 R |
|---|---|---|---|
| 4,012,367 | 3/1977 | Mazur | 260/112.5 R |

FOREIGN PATENT DOCUMENTS

| 1455176 | 5/1966 | France | 260/112.5 R |
|---|---|---|---|
| 1120755 | 4/1967 | United Kingdom | 260/112.5 R |

*Primary Examiner*—Delbert R. Phillips
*Attorney, Agent, or Firm*—Sughrue, Rothwell, Mion, Zinn and Macpeak

[57] ABSTRACT

The present invention relates to a method of treating diseases and particularly gastroduodenal ulcers linked to an hypersecretion of gastrin, and to polypeptide amide derivatives which can be used in this method as therapeutic agents and more specifically as antagonists of the action of gastrin and related polypeptides relative to their specific biological receptors.

This method comprises administering a therapeutically effective amount of a polypeptide amide derivative of general formula:

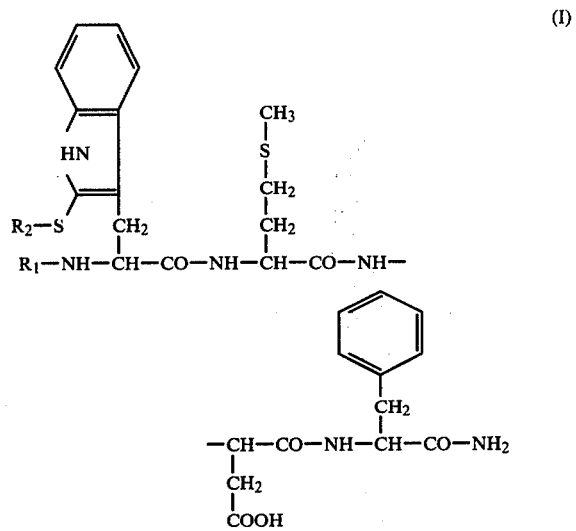

(I)

in which $R_1$ represents a hydrogen atom or an acyl radical and $R_2$ represents a substituted or unsubstituted aryl radical e.g. nitrophenyl group or dinitrophenyl group such as 2-nitrophenyl or 2-4-dinitrophenyl.

22 Claims, 6 Drawing Figures

MEDICAMENT WHICH ANTAGONIZES THE ACTION OF GASTRIN AND RELATED POLYPEPTIDES

BACKGROUND OF THE INVENTION

The present invention relates to novel medicaments comprising polypeptide amide derivatives, which can be used as therapeutic agents and more specifically as antagonists of the action of gastrin and related polypeptides relative to their specific biological receptors.

Gastrin is a natural hormone, which is in particular known for being responsible for the secretion of gastric juice. The way in which it acts on the organs of the digestive apparatus is, like that of most hormones, linked with the presence in said organs of target cells, whose plasma membranes have specific biological receptors able to fix the hormone molecules and produce under the action of the latter a cascade of biochemical reactions which lead to the synthesis and production of a particular product, such as gastric acid.

The term related polypeptides covers a family of polypeptides having at their end the sequence of four C terminal amino acids, L-tryptophanyl-L-methionyl-L-aspartyl-L-phenylalanine amide, characteristic of the biological activity of gastrin, whereby said polypeptides are able to produce biochemical reactions by fixing themselves to specific receptors.

It is known that a hormonal hypersecretion can cause certain known pathological disorders, for example for gastrin during the Zollinger-Ellison syndrome and suspected in numerous other ailments.

The difficulty occurring with the treatment of such pathological disorders is due to the fact that at present there is no product which is able to eliminate the action of these hormones relative to the target organs.

BRIEF SUMMARY OF THE INVENTION

The problem of the present invention is a medicament which makes it possible to eliminate the action of gastrin and related polypeptides by antagonism at their biological receptors.

This medicament comprises as active substance a polypeptide amide derivative of general formula:

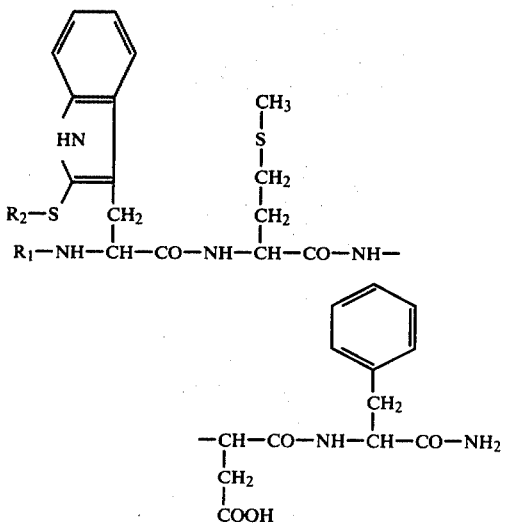

in which $R_1$ represents a hydrogen atom or an acyl radical and $R_2$ represents a substituted or unsubstituted aryl radical.

According to an advantageous characteristic of the invention $R_2$ is a nitrophenyl or a dinitrophenyl such as 2-nitrophenyl of formula:

or 2-4-dinitrophenyl of formula:

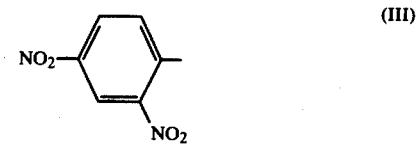

Another object of the present invention is to provide a method of treating deseases and particularly gastroduodenal ulcers linked to an hypersecretion of gastrin.

This method of treating gastroduodenal ulcers linked to an hypersecretion of gastrin comprises administering a therapeutically effective amount of a polypeptide amide derivative of general formula:

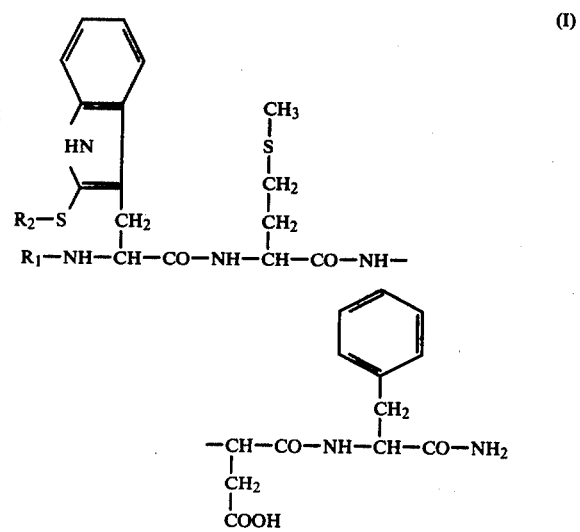

in which $R_1$ represents a hydrogen atom or an acyl radical and $R_2$ represents a substituted or unsubstituted aryl radical.

According to an advantageous characteristic of this method, the polypeptide amide derivative is a polypeptide amide derivative of general formula (I) in which $R_1$ represents a hydrogen atom or an acyl radical and $R_2$ is a nitrophenyl group or dinitrophenyl group such as 2-nitrophenyl of formula (II) or 2-4-dinitrophenyl of formula (III), preferably a 2-nitrophenyl.

The pharmaceutical properties of the polypeptide amide derivative defined by the general formula (I) hereinbefore are essentially due to the presence of the above sequence of four amino acids which are characteristic of gastrin and related polypeptides, and to the modification of this sequence by an arylthio radical such the orthonitrophenylthio or dinitrophenylthio radical in the 2-position of the indole nucleus of the tryptophanyl group of this sequence.

Thus, due to the presence of this modified sequence, the polypeptide amide derivative has the capacity of recognising the biological receptors of gastrin and related polypeptides and is fixed to the latter without simultaneously causing biochemical reactions.

Thus, although the radical $R_1$ of the above formula (I) has no limiting action in the activity of the polypeptide amide derivative it is obvious that the nature of this radical must not eliminate the capacity of the L-tryptophanyl-L-methionyl-L-aspartyl-L-phenylanyl amide sequence to recognise and be fixed to the biological receptors of gastrin and related polypeptides.

According to the invention the $R_1$ radicals are preferably radicals derived from an amino acid or one of its derivitives, such as the radicals: β-alanyl, glycyl, pyroglutamyl, N-benzoyl-glycyl, N-t-butyloxycarbonyl-L-glycyl, N-t-butyloxycarbonyl-L-alanyl, lysile and N-benzyloxy-carbonyl-L-prolyl, or radicals derived from a peptide or one of its derivitives such as for example: the radical L-pyroglutamyl-L-glycyl-L-prolyl-L-tryptophanyl*-L-leucyl-L-glutamyl-L-glutamyl-L-glutamyl-L-glutamyl-L-glutamyl-L-alanyl-L-tyrosyl-L-glycyl designated hereinafter by the term $R_{GI}$, the radical L-pyroglutamyl-L-glycyl-L-prolyl-L-tryptophanyl*-L-leucyl-L-glutamyl-L-glutamyl-L-glutamyl-L-glutamyl-L-glutamyl-L-alanyl-L-tyrosyl-(oxysulphonic in the 4-position of the phenyl nucleus) designated hereinafter by the term $R_{GII}$, the radical L-pyroglutamyl-L-glutamyl-L-aspartyl-L-tyrosyl-L-threonyl-L-glycyl, designated hereinafter by the term $R_C$, the radical N-t-butyloxycarbonyl-L-aspartyl-L-tyrosyl-L-methionyl-L-glycyl designated hereinafter by the term $R_{CCK}$, the radical L-pyroglutamyl-L-leucyl-L-glycyl-L-prolyl-L-glutaminyl-L-glycyl-L-histidyl-L-prolyl-L-seryl-L-leucyl-L-valyl-L-alanyl-L-aspartyl-L-prolyl-L-seryl-L-lysyl-L-lysyl-L-glutaminyl-L-glycyl-L-prolyl-L-tryptophanyl*-L-leucyl-L-glutamyl-L-glutamyl-L-glutamyl-L-gl tamyl-L-glutamyl-L-glutamyl-L-alanyl-L-tyrosyl-L-glycyl designated hereinafter by the term $R_{BGI}$, the radical L-leucyl-L-glutamyl-L-glutamyl-L-glutamyl-L-glutamyl-L-glutamyl-L-alanyl-L-tyrosyl-L-glycyl designated hereinafter by the term $R_{MGI}$, the radical L-leucyl-L-glutamyl-L-glutamyl-L-glutamyl-L-glutamyl-L-glutamyl-L-alanyl-L-tyrosyl (oxysulphonic in the 4-position of the phenyl nucleus)-L-glycyl, designated hereinafter by the term $R_{MGII}$.

In the radicals given hereinbefore the indication L-tryptophanyl followed by an asterisk (*) signifies that the tryptophanyl group is optionally substituted in the 2-position of its indole nucleus by a 2-nitrophenylthio radical.

$R_1$ may also represent a hydrogen atom or a radical chosen from among the alkylcarbonyl, arylcarbonyl, aralkylcarbonyl, alkoxycarbonyl, aryloxycarbonyl and aralkoxycarbonyl radicals.

As a non-limitative example of the polypeptide amide derivatives which can be used according to the invention reference can be made to the following compounds: orthonitrophenyl sulphenylated gastrin I, designated hereinafter by the gastrin term I-NPS, corresponding to the above general formula (I) in which $R_1$ stands for $R_{GI}$ and $R_2$ for the 2-nitrophenyl radical; orthonitrophenyl sulphenylated gastrin II, designated hereinafter by the gastrin term II-NPS which corresponds to the above general formula (I) in which $R_1$ stands for $R_{GII}$ and $R_2$ stands for the 2-nitrophenyl radical; orthonitrophenyl sulphenylated gastrin BIG which corresponds to the above general formula (I) with $R_1=R_{BGI}$ and $R_2=$2-nitrophenyl; orthonitrophenyl sulphenylated mini gastrin I or II corresponding to the above general formula (I) with $R_1=R_{MGI}$ or $R_{MGII}$ and $R_2=$2-nitrophenyl; orthonitrophenyl sulphenylated caerulein which corresponds to the above general formula (I) in which $R_1$ represents $R_C$ and $R_2$ the 2-nitrophenyl radical; orthonitrophenyl sulphenylated cholecystoquinone corresponding to the derivative of the above general formula (I) in which $R_1$ represents $R_{CCK}$ and $R_2$ the 2-nitrophenyl radical; orthonitrophenyl sulphenylated pentagastrin, designated hereinafter under the pentagastrin term NPS and which corresponds to the derivative of the above general formula (I) in which $R_1$ is the N-t-butyloxycarbonyl-glycyl radical and $R_2$ the 2-nitrophenyl radical.

The polypeptide amide derivatives can easily be obtained from the polypeptide amides of general formula:

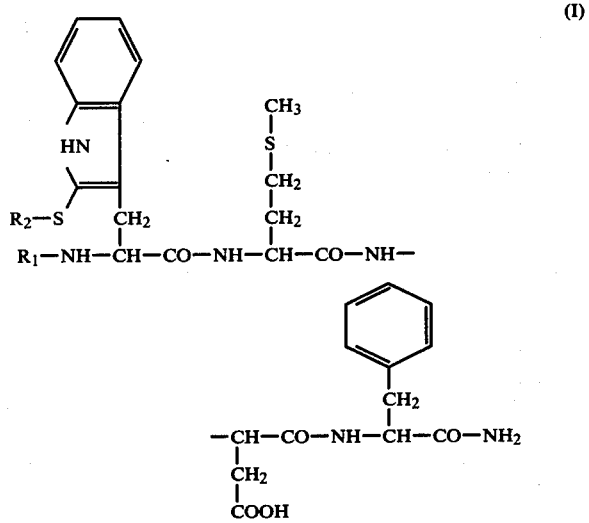

(I)

in which $R_1$ has the same meaning as hereinbefore, by reacting this polypeptide amide with a chloride of formula $R_2SCl$ in which $R_2$ has the same meaning as hereinbefore. For example, such derivatives can be obtained by reacting at ambient temperature in glacial acetic acid and protected from light an equimolar mixture of this polypeptide amide and 2-nitrophenyl-sulphenyl chloride or 2-4-dinitrophenyl-sulphenyl chloride of the following formulas:

(V)

or

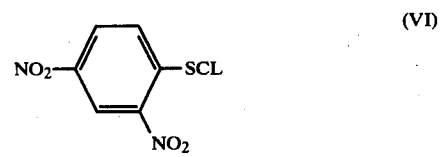

(VI)

During this reaction the mixture is continuously stirred and the development of the said reaction is controlled by measuring the optical density of the mixture at 280 or 365 nm. The stabilisation of the optical density of the mixture indicates that the reaction is complete.

As a non-limitative example the following polypeptide amide derivatives were prepared by this process: orthonitrophenyl sulphenylated gastrin I, orthonitrophenyl sulphenylated caerulein, orthonitrophenyl sulphenylated cholecystoquinone and orthonitrophenyl sulphenylated pentagastrin.

These derivatives are identified at the end of the reaction by their spectral characteristics, which are clearly differentiated relative to those of the starting constituents. Thus, polypeptide amide derivatives orthonitrophenyl sulphenylated on their tryptophanyl group have in visible light a maximum centred between 362 and 365 nm (with a molar $\epsilon$ of 3750–4450) and a minimum at about 317 nm; and in ultraviolet light a single very intense band at 280–281 nm (with a molar $\epsilon$ of 16,000–17,000) and a minimum at about 257 nm.

Moreover, thin layer chromatographic analysis of the products obtained in several solvent systems indicates that the mixture obtained at the end of the reaction only contains a single component.

The following table 1 gives the $R_F$ values which characterise the products obtained, being obtained by thin layer chromatography using a silica gel as the adsorbent and different solvent systems (columns I to IX) or cellulose as the adsorbent and a solvent system constituted by 75 parts of n-butanol, 10 parts of acetic acid and 25 parts of water (column X).

This table also shows the $R_F$ values which are characteristic of the initial polypeptide amides and orthonitrophenyl sulphenyl chloride, called NPS-Cl.

manner using the abbreviations conventionally adopted for designating amino acid residues:

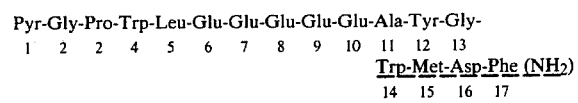

It should be noted that in this formula there are two Trp groups located respectively in the 4 N-terminal position and the 14 C-terminal position.

To check that the reaction has mainly taken placed on the Trp group in the 14-position this reaction is carried out using gastrin I tritiated on the tyrosinyl residue designated hereinafter by the term ($^3$H)Tyr and orthonitrophenyl sulphenyl chloride in a molar ratio 1:1.

The product obtained at the end of the reaction then undergoes enzymatic hydrolysis by the protease extracted from *Staphylococcus aureus*. This complete hydrolysis of the gastrin by the protease ensures the breaking of the polypeptide amide derivative between the glutamyl group in the 10-position and the alanyl group in the 11-position. In this way four sulphenylated or non-sulphenylated polypeptides are obtained, which are identified by their absorption in ultraviolet and visible light and by thin layer chromatography using silica gel as the adsorbent and different solvent systems. The polypeptides obtained are respectively:

PCA-Gly-Pro-Trp-Leu-Glu
PCA-Gly-Pro-Trp (NPS)-Leu-Glu
Ala-Tyr ($^3$H)-Gly-Trp-Met-Asp-Phe-NH$_2$
Ala-Tyr ($^3$H)-Gly-Trp (NPS)-Met-Asp-Phe-NH$_2$

The $R_F$ values characteristic of these polypeptides are

TABLE 1

| COMPOUNDS | I | II | III | IV | V | VI | VII | VIII | IX | X |
|---|---|---|---|---|---|---|---|---|---|---|
| NPS-Cl | 1.00 | 1.00 | 0.80 | 0.90 | 0.90 | — | — | 0.98 | 0.98 | 0.90–1.00 |
| Boc-Gly-Trp-Met-Asp-phe-NH$_2$ (pentagastrin) | 0.25 | 0.75–0.80 | 0.81 | 0.81 | 0.85 | — | — | — | — | 0.75 |
| Boc-Gly-Trp-(NPS)-Met-Aspe-Phe-NH$_2$ (Pentagastrin NPS) | 0.50–0.55 | 0.90 | — | 0.90 | 0.90 | — | — | — | — | 0.90 |
| Caerulein | 0.0 | 0.10 | — | 0.18–0.20 | 0.70–0.75 | 0.52 | 0.75 | — | — | 0.24–0.27 |
| Caerulein (NPS) | 0.0 | 0.20 | — | 0.27–0.30 | 0.75 | 0.68 | 0.80 | — | — | 0.30 |
| Gastrin I | — | — | — | 0.30–0.33 | 0.88 | — | — | 0.60–0.70 | 0.51 | — |
| Gastrin I (NPS) | — | — | — | — | — | — | — | 0.85 | 0.70–0.80 | — |
| Boc-Asp-Tyr-Met-Gly Trp-Met-Asp-Phe-NH$_2$ (Cholecystoguinone$^2$) | 0.07 | 0.58 | — | 0.88 | 0.91 | — | — | — | — | — |
| Boc-Asp-Tyr-Met-Gly-Trp (NPS)-Met-Asp-Phe-NH$_2$(cholecystoquinone NPS) | 0.13 | 0.63 | — | 0.83 | 0.81 | — | — | — | — | — |

I) silica gel F-(chloroform, benzene, acetic acid, ethanol: 85/10/5/20)
II) silica gel F-(ethyl acetate, pyridine, water, acetic acid: 60/60/60)
III) silica gel F (n-butanol, pyridine, water: 60/60/60)
IV) silica gel F (n-butanol, acetic acid, water: 75/10/25)
V) silica gel F (ethanol, water: 80/20)
VI) silica gel F (n-butanol, pyridine, acetic acid, water: 30/20/6/24)
VII) silica gel F (isopropanol, N-acetic acid: 80/40)
VIII) silica gel F (chloroform, methanol, 17% ammonia: 20/20/9)
IX) silica gel F acetonitrile, water: 3/1)
X) cellulose n-butanol, acetic acid, water: 75/10/35).

Moreover a supplementary check of the product obtained from gastrin I shows that the reaction between gastrin I and orthonitrophenly sulphenyl chloride essentially leads to the obtaining of the orthonitrophenyl sulphenylated derivative on the tryptophanyl group present in the sequence of four amino acids characteristic of the biological activity of gastrin.

Gastrin I is a heptadecapeptide having 17 amino acid residues. Its formula can be expressed in the following given in table 2.

TABLE 2

| Peptides obtained by hydrolysis of tritiated gastrin I NPS | $R_F$ of peptides in systems | | | | % radio-activity |
|---|---|---|---|---|---|
| | I | II | III | IV | |
| PCA-Gly-Pro-Trp-Leu-Glu | 0.13 | 0.70 | 0.66 | 0.39 | |
| PCA-Gly-Pro-Trp(NPS)-Leu-Glu | 0.19 | 0.72 | 0.87 | 0.41 | |
| Ala-($^3$H)Tyr-Gly-Trp-Met- | | | | | |

TABLE 2-continued

| Peptides obtained by hydrolysis of tritiated gastrin I NPS | $R_F$ of peptides in systems | | | | % radio-activity |
|---|---|---|---|---|---|
| | I | II | III | IV | |
| Asp-Phe-NH$_2$ | 0.25 | 0.96 | 0.82 | 0.83 | 15 ± 5 |
| Ala-($^3$H)Tyr-Gly-Trp-(NPS)-Met-Asp-Phe-NH$_2$ | 0.33 | 0.97 | 0.67 | 0.86 | 85 ± 5 |

(I) n-butanol, acetic acid, water : 75/10/25.
(II) Chloroform, methanol, 17% ammonia : 20/20/9.
(III) Ethanol, water : 80/20.
(IV) Acetonitrile, water : 3/1.

In addition the radioactivity of each of the products obtained is determined. The results of this measurement given in table 2 show a 15% radioactivity distribution on the peptide: Ala-($^3$H)Tyr-Gly-Trp-Met-Asp-Phe-NH$_2$ and 85% on the peptide: Ala-($^3$H)Tyr-Gly-Trp(NPS)-Met-Asp-Phe-NH$_2$.

Thus, the preparation process essentially leads to the orthonitrophenyl sulphenylated derivative on the tryptophanyl group located in the 14 C-terminal position.

The medicaments according to the invention have a remarkable stability. Thus, the polypeptide amide derivatives obtained, optionally purified by chromatography and distributed in cryotubes at a rate of 5 to 10 μg of product per 10 μl of glacial acetic acid can be kept for several months in liquid nitrogen (at −196° C.) without undergoing any change. Their spectral characteristics in ultraviolet and visible light are unchanged and their $R_F$ values determined by thin layer chromatography on stored products are identical to those of the starting products.

The medicaments according to the invention can be used as therapeutic agents for the treatment of pathological states such as the Zollinger-Ellison syndrome, gastroduodenal ulcers in their typical and atypical forms, gastric hypersecretion of intestinal resections and digestive capillary hemorrhages.

Moreover, the action of the medicament according to the invention can also take place on the transfer or secretion of water and electrolytes on the following organs: pancreas, liver, small intestine and Brunner's glands; on the enzymatic secretion (stomach, pancreas, small intestine); on the absorption of glucose, electrolytes and water relative to the small intestine; on the smooth muscular system, for example on organs stimulated by gastrin such as the lower oesophageal sphincter, the stomach, small intestine, colon and vesicle or on the organs which are inhibited by gastrin such as the pyloric sphincter, ileocaecal sphincter and Oddi's sphincter; on hormones liberated by gastrin such as insulin and calcitonin; on the blood circulation of the digestive organs such as the stomach, small intestine and pancreas; and on the trophic action of gastrin relative to a certain number of mucous membranes or organs such as the gastric mucosa, the mucous membrane of the small intestine and the pancreas.

The medicaments according to the invention can be administered in the form of injectable solutions by the intravenous route at a dose which is generally between 5 and 20 μg/kg.

A description will be provided hereinafter of tests which show the pharmacological properties of the medicaments according to the invention as an antagonist for the action of gastrin and related polypeptides with reference to target organs.

BRIEF DESCRIPTION OF THE DRAWINGS

The following description of the tests is provided in an illustrative and non-limitative form with reference to the attached drawings, wherein show.

DETAILED DESCRIPTION OF THE PREFERRED EMBODIMENTS

Figure 1:
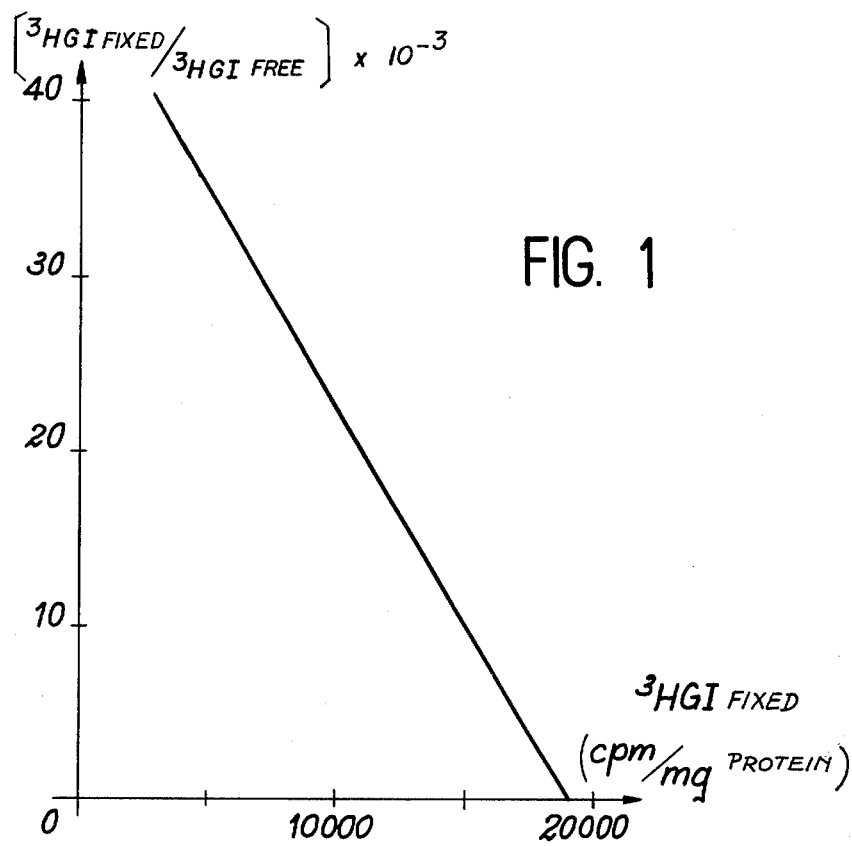
FIG. 1. A Scatchard representation of the link between tritiated gastrin I and its biological receptors.

The first test reveals the competitive action between human gastrin and the medicament according to the invention for the occupation of biological receptor sites of the gastrin by studying the link between gastrin and the plasma membranes of the fundus of the rat.

Initially plasma membranes were prepared from a male white rat of the Wistar CF strain weighing 250±50 g, stabilised beforehand for one month in an animal house by a standard feed of autoclaved biscuits 113 UAR. The rat, which did not fast prior to killing, was killed by a blow on the nape of the neck between 9 and 10 a.m. and was then laparotimized. The stomach was removed, opened in accordance with the greater curvature and washed in the following medium containing 0.25 M of saccharose, 30 nM of trihydroxymethylaminomethane - hydrochloric acid buffer at pH 7.4 and a temperature of 0° to 4° C. All the fundal mucosa (from the cardia to the antral junction) was scraped in a cold box using a glass blade and was collected in a medium containing 0.25 M of saccharose and 3 mM of trihydroxymethylaminomethane-hydrochloric acid buffer at pH 7.4 and a temperature of 0° to 4° C., whereby the volume of said medium was such that it approximately corresponded to 10 ml/g of tissue. The tissue was cut into fragments by means of scissors and homogenized in a rotary Potter-Elvejhem number C homogenizer rotating at 2,000 rpm with four up and down strokes of the piston.

The pulverised tissue obtained or homogenate was centrifuged in an Internationale PR2 refrigerated centrifuge with rotor number 269 for 6 minutes at a temperature of 4° C. and a speed of 1,000 r.p.m., i.e., centrifuging of 1,200 gxmn. The centrifugal mass was rinsed twice in a medium containing 0.25 M of saccharose and 3 mM of trihydroxymethylaminomethane-hydrochloric acid at pH 7.4 and a temperature of 0° to 4° C. The supernatant matter was combined and centrifuged in a Spinco L Beckman refrigerated ultracentrifuge with a 50 Ti rotor at 4° C. for 3 minutes at a speed of 12500 r.p.m. (28800 gxmn). The mass was washed twice in a medium containing 0.25 M of saccharose and 3 mM of trihydroxymethylaminomethane-hydrochloric acid buffer at pH 7.4 at a temperature of 0° to 4° C. The supernatant matter was combined and centrifuged in a Spinco L Beckman ultracentrifuge with a 50 Ti rotor for 30 minutes at a speed of 39,000 r.p.m. (2,770,000 gxmn). The mass obtained represents the total microsomes.

The microsomal mass was diluted in 50 ml of a medium containing 0.25 M of saccharose and 3 mM of trihydroxymethylaminomethane-hydrochloric acid buffer at pH 7.4 and a temperature of 0° to 4° C., after which it underwent zonal centrifuging in a Spinco 50 L Beckman refrigerated ultracentrifuge with Ti 14 roto in a 7% linear gradient (1.04 g/cm$^3$) at 60% (1.30 g/cm$^3$) of saccharose up to isopycnic equilibrium, i.e. 15 h at 20,000 r.p.m. and 4° C. After equilibration the gradient was collected in 25 ml fractions and the densities were determined by refractometry. The fraction whose density is between 1.12 and 1.14 g/cm$^3$ represents the fraction corresponding to the plasma membranes. It represents about 15 to 25% of the microsomal mass and is used on the same day that it is prepared.

During the preparation of the plasma membranes several determinations are performed on the homogenate obtained after fragmentation of the tissue and Potter homogenisation on the total microsomes and one the final fraction of the plasma membranes. These determinations are listed below: protein determination by the Lowry method (Lowry O. M., Rosembrorgh N. J., Farr A. L., Randall J. R.,: 1951, J. Biol. Chem. 193–265) with cattle albumin serum as the standard. ribonucleic acid determination according to the Schneider method (Schneider W. C., 1957, In: Method in Enzymology, Collowick and Kaplan Ed. Academic Press, New York, page 680). The substance (representing 5 mg of membrane protein) is precipitated by cold trichloroacetic acid (final concentration 7%) then centrifuged at 1,000 gxmn, washed 3 times with 10% trichloroacetic acid and then 3 times with 5 ml of 95% ethanol. The mass is hydrolysed for 30 minutes at a temperature of 90° C. in 2.5 ml of 5% trichloroacetic acid. The hydrolysate is centrifuged at 1,000 gxmn and the supernatant matter is coloured with orcinol, the absorption being 660 nm. phosphatases determination according to the Fiske and Subbarow method (Fiske C. H. and Subbarow Y.: 1925, J. Biol. Chem. 56: 375). The 5'-adenosine monophosphatases is determined by means of the following reagents: 2 mM of 5'-adenosine monophosphate, 100 mM of trihydroxymethylaminomethane-hydrochloric acid buffer at pH 7.5 and 0.6 mM of manganese chloride for 50 minutes at 37° C. The adenosine triphosphatase is determined by using the following reagents: 2 mM of sodium adenosine triphosphate, 100 mM of imidazole-hydrochloric acid at pH 8 and 2 mM of magnesium chloride for 10 minutes at 37° C. monoamine oxidase determination according to the method of Weissbach H., Smith T. E., Daly J. W., Witkop B., Undenfriend S., (1960, J. Biol. Chem. 235:1160) using the following reagents: 100 mM of kynuramine, 50 mM of potassium phosphate buffer at pH 7.4, by reading at 360 nm. cytochrome c oxydase determination according to the method of Cooperstein S. J., Lazarow A., (1951, J. Biol. Chem. 189:665) by means of the following reagents: 40 μm of reduced cytochrome c, 30 mM of potassium phosphate buffer at pH 7.4 and 1 mM of ethylene diamine tetraacetate at 25° C.

The oxidation kinetics are followed at 550 nanometers after adding membranes diluted in a solution of 1 mM of ethylene diamine tetraacetate, 1 mM of NaHCO$_3$ and 0.01% triton × 100.

The results of these determinations are given in table 3.

TABLE 3

| | 5' AMPase | ATPase | MAO | Cytochrome c oxydase in unit 3.1 Δ log$_{10}$ DOmin$^{-1}$/mg protein | Ribonucleic acid in g/mg protein |
|---|---|---|---|---|---|
| | in nmoles × min$^{-1}$/mg of protein | | | | |
| Homogenate Total | 6.4 | 199 | 420 | 74 | 53 |
| Microsomes | 16.7 | 417 | 760 | 60 | 80 |
| Plasma membranes density fraction 1.12 to 1.14 g/cm$^3$ | 57.1 | 1135 | 34 | 0 | 13 |

The figures given in the above table indicate the specific activities of the following enzymes: 5'-adenosinemonophosphatase (5' AMPase), adenosine triphosphatase (ATPase), monoamineoxydase (MAO) and cytochrome c oxydase, as well as the ribonucleic acid content.

These results show that the final fraction obtained corresponds to the plasma membranes. Compared with the homogenate this fraction is greatly enriched with the following enzymes: 5'-adenosinemonophosphatase and adenosine triphosphatase. However, it is greatly impoverished in cytochrome c oxydase, monoamineoxydase and ribonucleic acid i.e. in products coming from membranes with a mitochondrial origin or microsomes which carry ribosomes.

Examination of the final fraction obtained with the electronic microscope also confirms the fact that this fraction is enriched with plasma membranes.

The method is as follows: the membranes are fixed with 4% glutaraldehyde for 30 minutes at a temperature of 0° to 4° C. accompanied by stirring and are centrifuged for one hour in a Spinco Beckman ultracentrifuge with a 50 Ti rotor at a speed of 39,000 r.p.m. The mass is washed twice in a 50 mM buffered cacodylate solution at pH 7.4, dehydrated in alcohol and then included in an Epon mixture. The electronic microscope reveals vesicles with an average diameter of 0.2 microns and fragments of smooth membrane without any trace of mitochondria or mitochondria fragments or microsomes carrying ribosomes.

In addition, the cyclasic adenylate activity of the membranes is determined according to the Rosselin and Freychet method (Rosselin G., Freychet P.,: 1973, BBA 304:541–551) using the following reagents: 0.8 mM of adenosine triphosphate, 20 mM of creatine phosphate, 0.5 mg/ml of phosphokinase creatine, 5 mM of magnesium chloride, 10 mM of theophylline, 1 mM of ethylene diamine tetraacetate, 20 mM of trihydroxymethylaminomethane-hydrochloric acid buffer at pH 7.4 and in the presence of the following compounds: tritiated gastrin I, gastrin I or gastrin I-NPS at a dose of $10^{-8}$ M for a sample of 100 to 200 microgrammes of membrane proteins. The reaction takes place for 10 minutes at a temperature of 25° C. The results obtained are shown in table 4.

TABLE 4

| | base content of cyclic adenosine monophosphate pmoles min mg$^{-1}$ of protein | % stimulation | |
|---|---|---|---|
| | | Gastrin I | Tritiated Gastrin I |
| Homogenate | 3.2 | 53 | — |
| Total Microsomes | 5.4 | 94 | 83 |
| Plasma membranes density fraction 1.12 to 1.14 g/cm$^3$ | 9 | 277 | 178 |

For comparison purposes the table shows the results obtained for a determination of this type of the fractions corresponding to the one hand to the tissue homogenate and on the other to the total microsomes. These results show that the stimulation of the cyclasic adenyl activity by tritiated or non-tritiated gastrin I is much greater in the plasma membrane fraction than in the homogenate or total microsomes.

It is also clear that when this determination is carried out in the presence of gastrin I-NPS there is no stimulation of the cyclasic adenylate activity. It is thus established that the specific receptors of the gastrin are present in the plasma membranes obtained and that the enzyme of these receptors is not activated by the medicament according to the invention, that is to say gastrin I-NPS.

The quantities of tritiated gastrin I likely to become fixed to the plasma membranes are determined by using either tritiated gastrin I or a mixture of tritiated and non-tritiated gastrin I or a mixture of tritiated gastrin I and gastrin I-NPS.

In all cases the following procedure is used.

To 1.2 ml of plasma membrane containing 0.4 to 1 mg of proteins/ml are added 1.5 to 20 microliters of tritiated $10^{-6}$ M gastrin I, i.e., 15 to 150 μl of $10^{-6}$ M gastrin I-NPS, whereby to the mixture is added a buffer solution of 200 mM of trihydroxymethylaminomethane-hydrochloric acid at pH 7.4 in order to obtain a total volume of 1.5 ml. This mixture is maintained and constitutes the incubation medium at a temperature of 20±2° C. and samples are taken every minute for the first half hour from the successive 50 microliter samples. These samples are immediately diluted in 500 microliters of a stopping solution maintained at a temperature of 0° to 4° C., constituted by a buffer solution of 20 mM of trihydroxymethylaminomethane-hydrochloric acid at pH 7.4. The diluted sample is then filtered in vacuum until the filter has completely dried, after which the filter is placed in a liquid scintillation counting bottle containing 15 ml of PCS scintillating mixture. This bottle is agitated at laboratory temperature until the proteins have dissolved indicated by the translucid appearance of the membrane before being introduced into the scintillation counter.

The total specific radioactivity of the incubation medium is determined beforehand by sampling 10 microliters of this medium and introducing them directly, without filtration, into the counting bottle.

In addition, the absorption of the filter—plasma membrane system is determined by performing an incubation under the same conditions but without the plasma membrane, by introducing the latter, after dilution of the sample, into 500 microliters of the stopping solution. The thus performed radioactivity measurements make it possible to determine the tritiated gastrin quantity fixed on the plasma membranes and the tritiated gastrin quantity which is free in the incubation medium.

In a first experiment the incubation medium only contains tritiated gastrin I. The radioactivity measurements performed on successive samples taken every minute show that the tritiated gastrin I is fixed to the plasma membranes in saturable manner with an association constant $k_1 = 4.10^7$ M$^{-1}$mn$^{-1}$.

To establish whether this fixing is reversible the incubation medium is diluted by 10 at the fifteenth minute. At the end of this dilution successive 500 microliter samples are taken and are immediately filtered without being diluted in the stopping solution. The quantity of radioactivity fixed to the plasma membranes decreases in time, which shows that the fixing of the tritiated gastrin I to the plasma membranes is reversible with a disassociation constant k-1=0.35 mn$^{-1}$.

The Scatchard representation of the connection is illustrated in FIG. 1 and gives a single line. The maximum fixing capacity and the equilibrium constant are respectively $N = 42.10^{-14}$ moles/mg of membrane proteins and $k = 1.7.10^8$ M$^{-1}$.

In a second experiment the incubation medium contains both tritiated and non-tritiated gastrin I. The radioactivity measurements performed on successive samples show that for a same initial content of tritiated gastrin I the tritiated quantity of gastrin I fixed to the plasma membranes is smaller when the incubation medium also contains non-tritiated gastrin I. Thus, gastrin I is in competition with tritiated gastrin I for the occupation of the receptors.

TABLE 5

| Gastrin I in moles | Tritiated Gastrin I in moles | Fixed Tritiated Gastrin I (moles/mg of protein) |
|---|---|---|
| 0 | 0.9.10$^{-8}$ | 20.2.10$^{-14}$ |
| 0 | 1.8.10$^{-8}$ | 29.5.10$^{-14}$ |
| 0.9.10$^{-8}$ | 0.9.10$^{-8}$ | 12.1.10$^{-14}$ |

Table 5 shows the quantities of tritiated gastrin I fixed in equilibrium to the plasma membranes when the incubation medium contains 0.7 mg/ml of plasma membranes, in the case of tritiated gastrin I only, as well as tritiated gastrin I and non-tritiated gastrin I.

In a third experiment the incubation medium contains tritiated gastrin I and gastrin I-NPS. The concentration of tritiated gastrin I is $10^{-8}$ M and the concentration of gastrin I-NPS is $2.10^{-8}$ M. The radioactivity measurements performed on successive samples sampled every minute show that the quantity of tritiated gastrin I fixed to the plasma membranes is lower in the presence of gastrin I-NPS.

Figure 2:
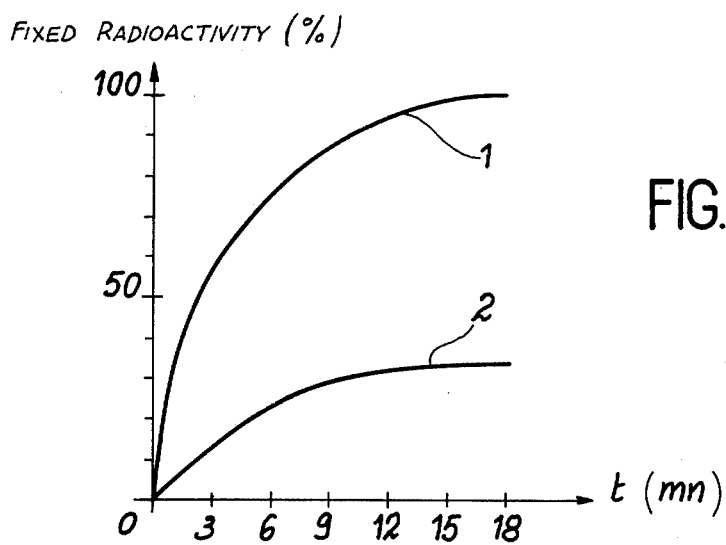
FIG. 2. A graph showing the level of tritiated gastrin I fixed to the biological receptors as a function of time.

FIG. 2 illustrates the results obtained relative to the values of the radioactivity fixed to the plasma membranes as a function of time, both when the medium contains only tritiated gastrin I (curve 1) and when the medium contains tritiated gastrin I and gastrin I-NPS (curve 2). It can be seen that curve 2 has an equilibrium plateau at a value well below that of curve 1, said value being reduced by about 70% compared with that of curve 1. In the presence of gastrin I-NPS the quantity of fixed gastrin I is proportional to the gastrin I content of the gastrin I/gastrin I-NPS mixture.

In a fourth experiment the quantities of radioactivity fixed in equilibrium were determined for tritiated gastrin concentrations varying from $2.10^{-9}$ M to $2.10^{-8}$ M, both in the absence of gastrin I-NPS and in the presence of gastrin I-NPS $2.10^{-8}$ or $10^{-8}$ M.

Figure 3:
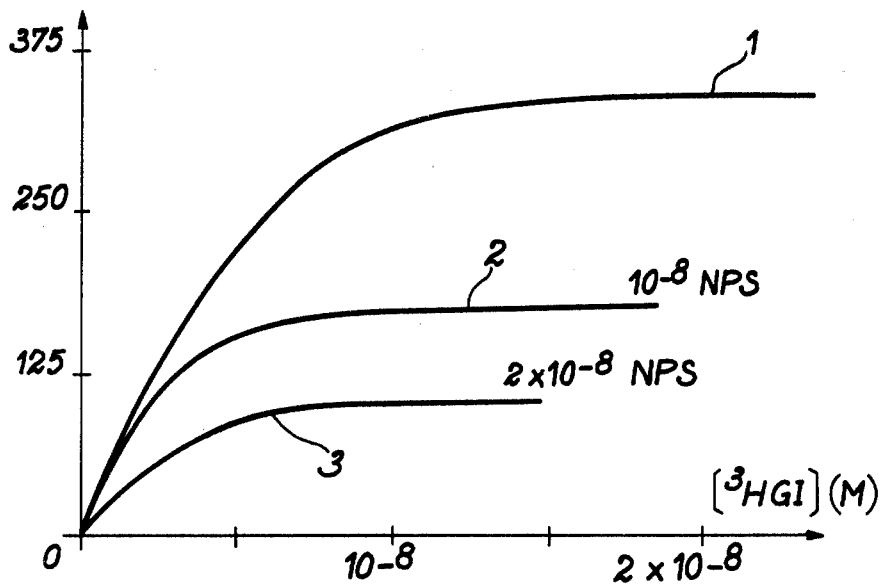
FIG. 3. A graph of the quantity of tritiated gastrin I fixed to biological receptors as a function of the initial content of tritiated gastrin I of a mixture of tritiated gastrin I and gastrin I NPS.

The results obtained are given in FIG. 3 which shows the curves of fixed radioactivity in equilibrium as a function of the tritiated gastrin I concentration. Curve 1 is obtained for gastrin I only, curve 2 for gastrin I in the presence of gastrin I-NPS $10^{-8}$ M and curve 3 for gastrin I in the presence of gastrin I-NPS $2.10^{-8}$ M.

Examination of these curves shows that the decrease of the fixed radioactivity in equilibrium is proportional to the decrease of the gastrin I concentration in the gastrin I/gastrin I-NPS mixture.

The second test comprises two series of experiments which serve to show that the medicaments according to the invention have an inhibiting action on the stimulated secretion of gastric juice.

A first series of experiments was carried out on male Wistar rats weighing 300 to 325 g. The procedure used was that of Ghosh and Schild, modified by Lai. The rats fasted for the 18 hours preceding the test. On the day of the test the rats were anaesthesized with urethane by the intraperitoneal route at a rate of 1.20 g of urethane per kilogramme. The rectal temperature was maintained at $34°\pm1°$ C. by means of an anal probe connected to a thermometer which electronically controlled the lighting up of a 100 Watt lamp positioned above each rat. An oesophageal probe (polyethylene catheter) was introduced up to the oesophagus—rumen junction of the rat and another catheter was introduced into the pyloric opening via the duodenum. The stomach was perfused with a solution of physiological serum introduced by means of the oesophageal tube at a constant speed of 1 ml/mn and was collected every ten minutes by the pyloroduodenal probe.

The rats prepared in this way were left to rest for a period of at least 45 minutes. The perfusate sampled every 10 minutes was then determined by means of a 0.01 N soda solution at pH 8.45, corresponding to a phenolphthalein colour change or at pH 7.4 with an automatic titration apparatus at constant pH.

After determining the basal acid secretion of the gastric juice on at least four consecutive samples a dose of gastrin was intravenously administered to the rats in the vein of the penis and subsequently the response to this stimulation was recorded until the secretion returned to the basal level over a period of at least twice 10 minutes. These injections were repeated at intervals which are a minimum of 90 minutes with different doses of gastrin I or with doses of gastrin I associated with the medicament according to the invention, whereby in the case of gastrin I-NPS the secretory response is recorded at the end of each injection. In the case of gastrin I the doses are 50, 100, 200, 400 and 800 ng per rat and in the case of gastrin I-NPS 50, 100 and 200 ng per rat, associated with each dose of gastrin I. The animals are placed in groups of four to six rats. The results are expressed in microequivalents of hydrochloric acid per 40 minutes and are calculated as follows: either as the number of secreted microequivalents after stimulation less the number of microequivalents secreted in the 40 minutes prior to the injection of the dose, or as an acid peak, i.e., taking the average of the two consecutive maximum responses for each dose less the average value for the two basal values preceding the injection.

The mean values of the secretion obtained for each dose of gastrin I and each dose of gastrin I associated with a dose of gastrin I-NPS make it possible to establish the dose—response curves of the gastric secretion as a function of the injected products. The transformation into double inverse makes it possible by analogy with enzymatic reactions to conclude whether the inhibition is of the competitive type or not.

Figure 4:
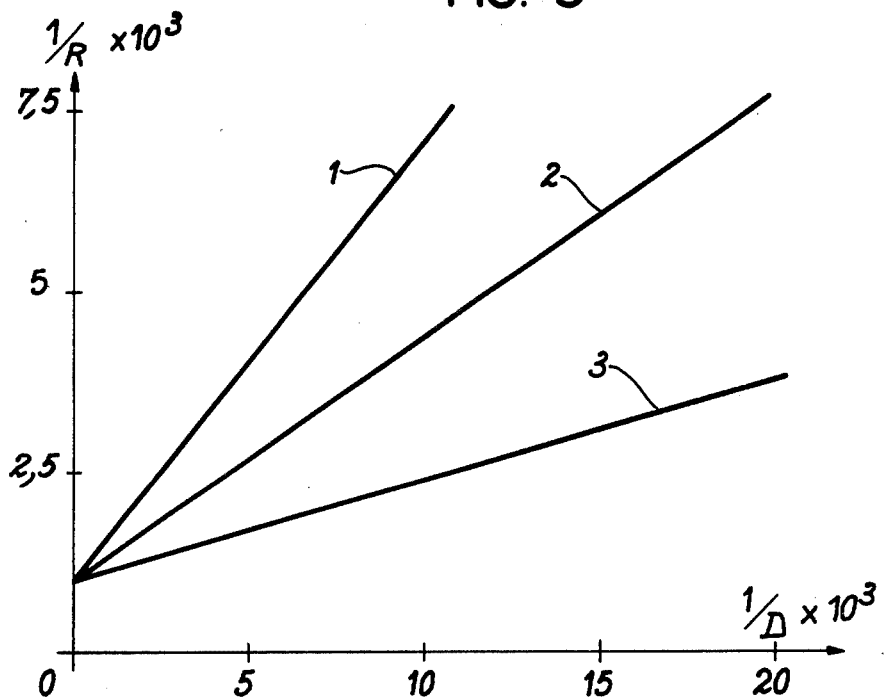
FIG. 4. A double inverse representation of the secreted gastric acid quantity as a function of the injected gastrin dose in ng.

FIG. 4 illustrates the results obtained, whereby the abscissa carries the inverse of the gastrin doses, the doses being expressed in nanogrammes and in the ordinate the inverse of the response to stimulation, said response being expressed in microequivalents of hydrochloric acid. The straight line 1 indicates the responses obtained for variable doses of gastrin I alone, whilst straight line 2 illustrates the responses obtained when 100 ng of gastrin I-NPS were associated with the different doses of gastrin I, whilst curve 3 illustrates the responses obtained when 200 ng of gastrin I-NPS are associated with each dose of gastrin I. The 3 curves converge at the same point, showing that inhibition is competitive. It is also apparent that the higher the concentration of gastrin I-NPS the lower the responses obtained.

Table 6 illustrates the results relative to the percentage inhibition obtained by associating 50, 100, 150 and 200 ng of gastrin I with a dose of 50 ng of gastrin NPS, i.e. doses in a ratio of 1:1, 1:2, 1:3 and 1:4.

TABLE 6

| Ratio of concentrations gastrin I-NPS/ gastrin I | 1/1 | 1/2 | 1/3 | 1/4 |
|---|---|---|---|---|
| % inhibition | 100 | 75 | 65 | <35 |

On performing the same series of experiments with pentagastrin-NPS associated with pentagastrin it is found that pentagastrin-NPS inhibits the pentagastrin action.

Table 7 indicates the results relative to the percentage inhibition obtained on associating 50, 100, 150 and 200 ng of pentagastrin with a dose of 50 ng of pentagastrin-NPS, i.e. doses in ratios 1:1, 1:2, 1:3 and 1:4.

TABLE 7

| Concentration ratio pentagastrin-NPS/ pentagastrin | 1/1 | 1/2 | 1/3 | 1/4 |
|---|---|---|---|---|
| % inhibiton | 100 | 100 | 75 | <20 |

In a second series of experiments an intravenous perfusion of an isotonic solution of 9% sodium chloride was administered at a rate of 2.4 ml/h to rats prepared in the manner indicated hereinbefore according to the procedure of Ghosh and Schild, modified by Lai. This perfusion was administered to the vein of the penis.

The rats prepared in this manner were left at rest for at least 45 minutes, then the acidity was determined as hereinbefore on the gastric perfusate sampled every 10 minutes. After one hour of basal secretion gastrin I-NPS was added to the perfusion in such a way that a given dose of the medicament according to the invention was continuously passed into the perfusion for a period of 3 hours. At the end of the first hour a dose of gastrin I was added to the perfusion. The results obtained are given in FIG. 5a showing the variations of the gastric secretion as a function of time. It can be seen that the addition of I-NPS gastrin to the perfusion at a dose of 100 ng/h causes no secretory response and that the consecutive addition of 200 or 400 ng/h of gastrin I progressively re-establishes a stimulated secretion plateau.

Figure 5B:
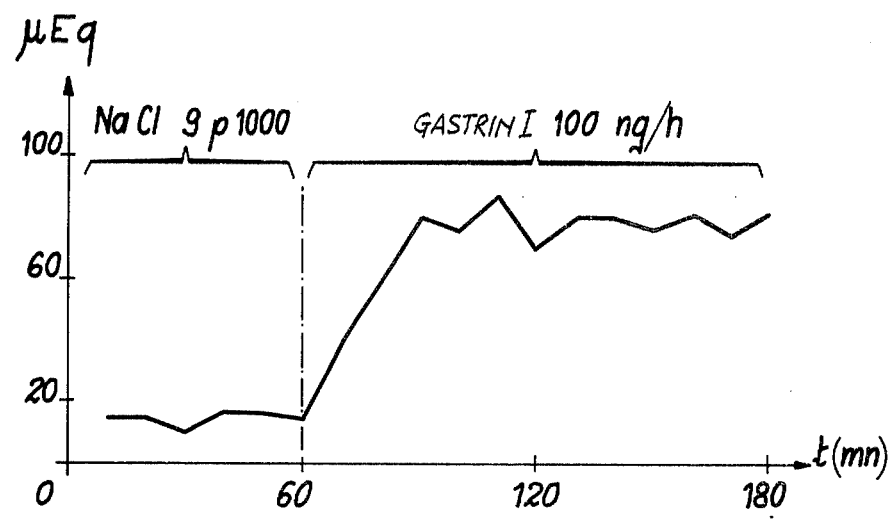
FIG. 5b. The gastric acid secretory response as a function of time during the injection of gastrin I alone.
Figure 5A:
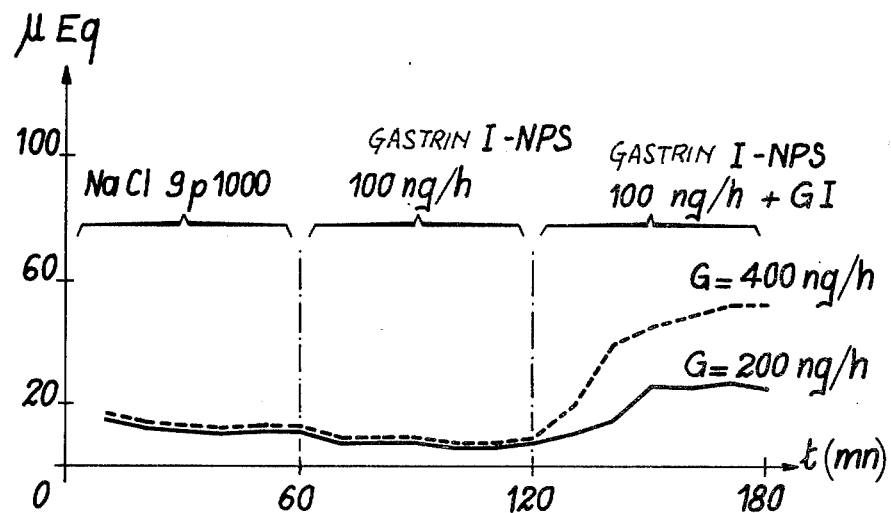
FIG. 5a. The gastric acid secretory response as a function of time and the injected products (gastrin I and gastrin I-NPS).

FIG. 5b shows for comparison purposes the results obtained for a continuous perfusion of 100 ng/h of gastrin I.

The comparison of the curves obtained shows that the stimulated secretion plateau by associating 100 ng/h of Gastrin I-NPS with 400 ng/h of gastrin I reaches the level of 100 ng/h of gastrin I 40 minutes after the introduction of gastrin I into the perfusion. On associating 200 ng/h of gastrin I with 100 ng/h of gastrin I-NPS the plateau is obtained at a lower level 30 minutes after the introduction of gastrin I into the perfusion.

These results show that an equilibrium is established between the quantities of gastrin I and gastrin I-NPS fixed to the receptors and that the gastrin I-NPS can be displaced by gastrin I.

We shall now describe the test results of the pentagastrin (pentagastrin NPS) orthonitrophenyl sulphenylated derivative acute toxicity on mice.

Male mice weighing 30 g are injected pentagastrin NPS by the intraperitoneal route in a volume of 1 to 2 ml, at doses of: 160, 320, 640, 1280 and 2560 μg/kg, which represent 20 to 320 times the dose giving the maximum acid response in the rat (8 μg/kg).

Each dose is injected to a group of ten mice and the death rate is controlled 1 h, 2 h, 6 h, 12 h, 24 and 48 h after the injection of pentagastrin NPS.

All the dead or surviving animals are autopsied, the stomach and the small intestine are examined for heamorrhages or ulcers.

The results obtained are shown in the following table I which indicates the number of death cases observed in each group of mice treated.

Table I

| Pentagastrine NPS-dose μg/kg | 1 h | 2 h | 6 h | 12 h | 24 h | 48 h |
|---|---|---|---|---|---|---|
| 160 | | | | | | |
| 320 | | | | | | |
| 640 | | | | | | |
| 1280 | | | | | 1 | |
| 2560 | | | | 1 | 1 | 2 |

Giving pentagastrin NPS at the above mentioned doses does not lead to any digestive hemorrhage in the mouse, yet a few petechiae are observed in mice which were given a dose of 2560 μg/kg pentagastrin NPS.

As a comparison, the same test of acute toxicity was done on pentagastrin in the same conditions.

The results obtained are shown in the following table 2.

Table 2

| Pentagastrine dose μg/kg | 1 h | 2 h | 6 h | 12 h | 24 h | 48 h |
|---|---|---|---|---|---|---|
| 160 | | | | | | |
| 320 | | | | | | |
| 640 | | | | | | |
| 1280 | | 1 | 1 | | | |
| 2560 | | 2 | | | | 1 |

Digestive hemorrhages are observed the importance of which increases with the dose when pentagastrin is given at a dose of 320 μg/kg or above.

Thus giving pentagastrin NPS at doses under 2,5 mg/kg leads to no modifications (petechiae) of the stomach and of the intestine whereas pentagastrin leads to digestive hemorrhages at a dose of 320 μg/kg or above.

The LD 50 of pentagastrin NPS was calculated by the following method.

The lethality observed not exceeding in 24 hours 20% of the animals, for the determination of the LD 50 a logit-log paper was used on which abcissae represented the doses given (log) and ordinates the "probits" of death cases observed. It was thus found that the LD 50 of the pentagastrin NPS is higher than 3.2 mg/kg.

The LD 50 of pentagastrin calculated in the same conditions is also higher than 3.2 mg/kg.

The invention is not limited to the embodiments described and represented hereinbefore and various modifications can be made thereto without passing beyond the scope of the invention.

What is claimed is:

1. A medicament, which comprises as active substance a polypeptide amide derivative of general formula:

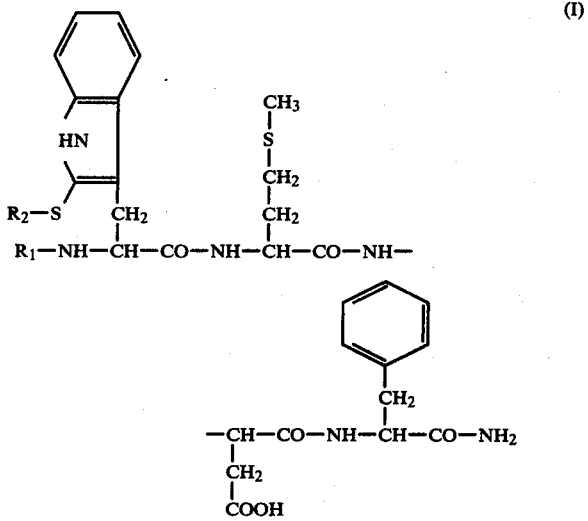

in which $R_1$ represents a hydrogen atom, an amino acid radical, a N-t-butyloxycarbonyl-L-amino acid radical, a N-benzyloxycarbonyl amino acid radical or a N-benzoyl amino acid radical, wherein the term amino acid radical means an amino acid radical selected from the group consisting of β-alanyl, glycyl, pyroglutamyl, N-benzoyl glycyl, N-t-butyloxycarbonyl-L-glycyl, N-t-butyloxycarbonyl-L-alanyl, lysile and N benzyloxy-carbonyl-L-propyl or a peptide radical selected from the group consisting of:
L-pyroglutamyl-L-glycyl-L-prolyl-L-tryptophanyl-L-leucyl-L-glutamyl-L-glutamyl-L-glutamyl-L-glutamyl-L-glutamyl-L-alanyl-L-tyrosyl-L-glycyl,
L-pyroglutamyl-L-glycyl-L-propyl-L-typtophanyl L-leucyl-L-glutamyl-L-glutamyl-L-glutamyl-L-glutamyl-L-glutamyl-L-alanyl-L-tyrosyl-(oxysulphonic in the 4-position of the phenyl nucleus),
L-pyroglutamyl-L-glutamyl-L-aspartyl-L-tyrosyl-L-threonyl-L-glucyl, N-t-butyloxycarbonyl-L-aspartyl-L-tyrosyl-L-methionyl-L-glycyl,
L-pyroglutamyl-L-leucyl-L-glycyl-L-prolyl-L-glutaminyl-L-glycyl-L-histidyl-L-prolyl-L-seryl- L-leucyl-L-valyl-L-alanyl-L-aspartyl-L-prolyl-L-seryl-L-lysyl-L-lysyl-L-glutaminyl-L-glycyl-L-propyl-L-tryptophanyl-L-leucyl-L-glutamyl-L-glutamyl-L-glutamyl-L-glu amyl-L-glutamyl-L-glutamyl-L-alanyl-L-tyrosyl-L-glycyl, L-leucyl-L-glutamyl-L-glutamyl-L-glutamyl-L-glutamyl-L-glutamyl-L-alanyl-L-tyrosyl-L-glycyl, and L-leucyl-L-glutamyl-L-glutamyl-L-glutamyl-L-glutamyl-L-glutamyl-L-alanyl-L-tyrosyl-(oxysulphonic in the 4-position of the phenyl nucleus)-L-glycyl, and $R_2$ represents 2-nitrophenyl or 2,4-dinitrophenyl.

2. A medicament according to claim 1, wherein $R_2$ is 2-nitrophenyl.

3. A medicament according to claim 1 wherein $R_2$ is 2-4-dinitrophenyl.

4. A medicament according to claim 1, wherein $R_1$ is an acyl radical chosen from the group comprising N-t-butyloxycarbonylbeta-alanyl, N-t-butyloxycarbonylglycyl, beta-alanyl and glycyl.

5. A medicament according to claim 4 wherein $R_1$ is N-t-butyloxycarbonyl-$\beta$-alanyl and $R_2$ is 2-nitrophenyl.

6. The medicament of claim 1 wherein $R_1$ is a hydrogen atom and $R_2$ is 2-nitrophenyl.

7. The medicament of claim 4 wherein $R_1$ is N-t-butyoxycarbonyl-L-glycyl and $R_2$ is 2-nitrophenyl.

8. The medicament of claim 1 wherein $R_1$ is a hydrogen atom and $R_2$ is 2-nitrophenyl.

9. A medicament according to claim 1, wherein the polypeptide amide derivative is orthonitrophenyl sulphenylated gastrin in the 2-position of the indole nucleus of its tryptophanyl groups.

10. A medicament according to claim 1, wherein the polypeptide amide derivative is orthonitrophenyl sulphenylated gastrin in the 2-position of the indole nucleus of its tryptophanyl group connected to the methionyl group.

11. A medicament according to claim 1, wherein the said polypeptide amide derivative is orthonitrophenyl sulphenylated caerulein in the 2-position of the indole nucleus of its tryptophanyl group.

12. A medicament according to claim 1, wherein the polypeptide amide derivative is orthonitrophenyl sulphenylated cholecystoquinone in the 2-position of the indole nucleus of its tryptophanyl group.

13. A method of treating gastroduodenal ulcers linked to an hypersecretion of gastrin which comprises administering a therapeutically effective amount of a polypeptide amide derivative of general formula:

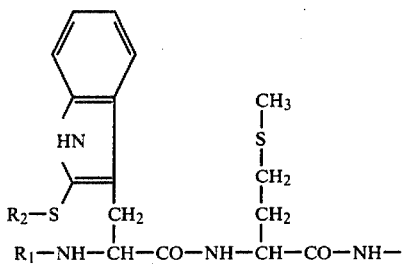

(I)

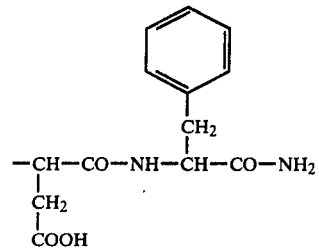

in which $R_1$ represents a hydrogen atom, an amino acid radical, a N-t-butyloxycarbonyl-L-amino acid radical, a N-benzyloxycarbonyl amino acid radical or a N-benzoyl amino acid radical, wherein the term amino acid radical means an amino acid radical selected from the group consisting of $\beta$-alanyl, glycyl, pyroglutamyl, N-benzoyl glycyl, N-t-butyl-oxycarbonyl-L-glycyl, N-t-butyloxycarbonyl-L-alanyl, lysile and N benzyloxy-carbonyl-L-prolyl or a peptide radical selected from the group consisting of:

L-pyroglutamyl-L-glycyl-L-propyl-L-tryptophanyl-L-leucyl-L-glutamyl-L-glutamyl-L-glutamyl-L-glutamyl-L-glutamyl-L-alanyl-L-tyrosyl-L-glycyl, L-pyroglutamyl-L-glycyl-L-propyl-L-tryptophanyl L-leucyl-L-glutamyl-L-glutamyl-L-glutamyl-L-glutamyl-L-glutamyl-L-alanyl-L-tyrosyl-(oxysulphonic in the 4-position of the phenyl nucleus), L-pyroglutamyl-L-glutamyl-L-aspartyl-L-tyrosyl-L-threonyl-L-glycyl, N-t-butyloxycarbonyl-L-aspartyl-L-tyrosyl-L-methionyl-L-glycyl, L-pyroglutamyl-L-leucyl-L-glycyl-L-prolyl-L-glutaminyl-L-glycyl-L-histidyl-L-prolyl-L-seryl-L-leucyl-L-valyl-L-alanyl-L-aspartyl-L-prolyl-L-seryl-L-lysyl-L-lysyl-L-glutaminyl-L-glycyl-L-prolyl-L-tryptophanyl-L-leucyl-L-glutamyl-L-glutamyl-L-glutamyl-L-glu amyl-L-glutamyl-L-glutamyl-L-alanyl-L-tyrosyl-L-glycyl, L-leucyl-L-glutamyl-L-glutamyl-L-glutamyl-L-glutamyl-L-glutamyl-L-alanyl-L-tyrosyl-L-glycyl, and L-leucyl-L-glutamyl-L-glutamyl-L-glutamyl-L-glutamyl-L-glutamyl-L-alanyl-L-tyrosyl-(oxysulphonic in the 4-position of the phenyl nucleus)-L-glycyl and $R_2$ represents 2-nitrophenyl or 2,4-dinitrophenyl.

14. A method according to claim 13, wherein the polypeptide amide derivative is a polypeptide amide derivative of general formula (I) in which $R_2$ is a 2-nitrophenyl group.

15. A method according to claim 13, wherein the polypeptide amide derivative is a polypeptide amide derivative of general formula (I) in which $R_2$ is a 2-4-dinitrophenyl group.

16. A method according to claim 13, wherein the polypeptide amide derivative is a polypeptide amide derivative of general formula (I) in which $R_1$ is an acyl radical chosen from the group comprising N-t-butyloxycarbonyl-beta-alanyl, N-t-butyloxycarbonylglycyl, beta-alanyl and glycyl.

17. A method according to claim 13, wherein the polypeptide amide derivative is orthonitrophenyl sulphenylated gastrin in the 2-position of the indole nucleus of its tryptophanyl groups.

18. A method according to claim 13, wherein the polypeptide amide derivative is orthonitrophenyl sulphenylated gastrin in the 2-position of the indole nucleus of its tryptophanyl group connected to the methionyl group.

19. A method according to claim 13, wherein the polypeptide amide derivative is orthonitrophenyl sulphenylated caerulein in the 2-position of the indole nucleus of its tryptophanyl group.

20. A method according to claim 13, wherein the polypeptide amide derivative is orthonitrophenyl sulphenylated cholecystoquinone in the 2-position of the indole nucleus of its tryptophanyl group.

21. A medicament according to claim 13 wherein $R_1$ is N-t-butyloxycarbonyl-$\beta$-alanyl and $R_2$ is 2-nitrophenyl.

22. The medicament of claim 13 wherein $R_1$ is N-t-butyoxycarbonyl-L-glycyl and $R_2$ is 2-nitrophenyl.

* * * * *